(12) United States Patent
Hilliard (10) Patent No.: US 8,060,236 B2
(45) Date of Patent: Nov. 15, 2011

(54) SYSTEM FOR PRODUCING ORTHODONTIC ALIGNERS BY CNC MACHINING

(76) Inventor: Jack Keith Hilliard, Lakeland, FL (US)

(*) Notice: Subject to any disclaimer, the term of this patent is extended or adjusted under 35 U.S.C. 154(b) by 865 days.

(21) Appl. No.: 11/871,487

(22) Filed: Oct. 12, 2007

(65) Prior Publication Data

US 2008/0254402 A1 Oct. 16, 2008

Related U.S. Application Data

(60) Provisional application No. 60/829,558, filed on Oct. 16, 2006.

(51) Int. Cl.
*G06F 19/00* (2011.01)
*A61C 5/08* (2006.01)

(52) U.S. Cl. .......... 700/160; 700/118; 700/98; 700/163; 700/182; 433/218; 433/223

(58) Field of Classification Search ............... 29/896.1; 700/160, 118, 98, 163, 182; 433/218, 223
See application file for complete search history.

(56) References Cited

U.S. PATENT DOCUMENTS

| | | | |
|---|---|---|---|
| 5,139,419 A | 8/1992 | Andreiko et al. | |
| 5,447,432 A | 9/1995 | Andreiko et al. | |
| 5,683,243 A | 11/1997 | Andreiko et al. | |
| 5,975,893 A | 11/1999 | Chishti et al. | |
| 6,293,790 B1 | 9/2001 | Hilliard | |
| 6,398,548 B1 | 6/2002 | Muhammad et al. | |
| 6,471,511 B1 * | 10/2002 | Chishti et al. | 433/24 |
| 6,616,444 B2 | 9/2003 | Andreiko et al. | |
| 6,702,575 B2 | 3/2004 | Hilliard | |
| 6,928,733 B2 | 8/2005 | Rubbert et al. | |
| 7,077,646 B2 * | 7/2006 | Hilliard | 433/6 |
| 7,261,533 B2 * | 8/2007 | Wrosz et al. | 425/110 |
| 7,572,121 B2 * | 8/2009 | Wrosz et al. | 425/110 |
| 2004/0115586 A1 | 6/2004 | Andreiko et al. | |
| 2006/0093982 A1 * | 5/2006 | Wen | 433/6 |
| 2007/0178423 A1 | 8/2007 | Rubbert et al. | |

* cited by examiner

*Primary Examiner* — Albert Decady
*Assistant Examiner* — Sunray Chang
(74) *Attorney, Agent, or Firm* — Dorr, Carson & Birney, P.C.

(57) ABSTRACT

A system produces orthodontic aligners by CNC machining. A digital model of the patient's dental anatomy is manipulated using CAD software to create a solid CAD model of an aligner. A CNC milling machine is then used to machine the inside and outside surfaces of the aligner from a block of suitable material. A progressive series of aligners can also be designed.

6 Claims, 7 Drawing Sheets

SYSTEM FOR PRODUCING ORTHODONTIC ALIGNERS BY CNC MACHINING

RELATED APPLICATION

The present application is based on and claims priority to the Applicant's U.S. Provisional Patent Application 60/829,558, entitled "System for Producing Orthodontic Aligners by CNC Machining," filed on Oct. 16, 2006.

BACKGROUND OF THE INVENTION

1. Field of the Invention

The present invention relates generally to the field of orthodontics. More specifically, the present invention discloses a system for producing orthodontic aligners by CNC machining.

2. Statement of the Problem

The infiltration into dentistry of new computer-based processes involving 3D imaging of human teeth began in the early 1990's. Particularly in orthodontics, these new digital technologies are providing orthodontists with fundamentally new tools for delivering orthodontic treatment. Early patents in this field such as U.S. Pat. No. 5,139,419 to Andreiko et. al. described the early methods for the 3D imaging of teeth. The subsequent manipulation of virtual occlusion to obtain information necessary for orthodontically correcting tooth position according to a virtually-determined ideal has been a key step in advancing the standard of care within orthodontics. In recent years laboratory processes related to the 3D imaging of a patient's dentition have continued to expand and have served as the basis for the provision of a number of new commercial services that have become available to orthodontists.

An example of the successful orthodontic application of these digital technologies is seen in the commercial service known as the Invisalign program. The Invisalign program is based on U.S. Pat. No. 5,975,893 (Chishti et al.), and many related patents including in particular U.S. Pat. No. 6,398,548. The Invisalign program is described in full detail below because it illustrates all of the technical aspects of digital applications within orthodontics. It illustrates the business aspects of new digital services, and it depicts the advantages of new types of technology being introduced into the practice of orthodontics. The current invention accommodates or impacts many of these areas. To follow then is an exhaustive description of the Invisalign program to best contrast the description of the improvements and advantages provided by the present invention that follows.

The Invisalign program involves the creation of a patient's virtually treated finished occlusion. This is the finished or ideal occlusion produced strictly within the confines of computer software that can be displayed on a computer monitor. From that, output methodologies are used to fabricate a series of progressive polymeric tooth positioners. Invisalign positioners, called aligners, are generally similar in appearance to appliances known as mouth guards worn by sports participants or the soft plastic appliances worn at night to protect teeth against the destructive effects of bruxism. The Invisalign program is marketed to the general public as an improved alternative to conventional orthodontic braces and is referred to in TV advertising as "invisible braces."

Invisalign tooth positioners are thin, transparent U-shaped plastic appliances formed over computer-generated physical forming patterns grown from the virtual model of the virtual teeth described above. The process for forming aligners uses a combination of vacuum, pressure and heat. This forming process is informally referred to within the orthodontic laboratory community as the "suck down" process and as such, aligners are informally considered to be suck-down-type appliances.

The Invisalign-type tooth aligners are formed from a thinner material than the traditional mouth guard-type appliance. One commonly used material known as polycarbonate (PC) is a harder but still relatively flexible and somewhat elastic polymeric material. Other materials such as co-polymers including ethylene vinyl acetate and polypropylene as well as polypropylene alone, and other olefin-type plastics are also used for sucking-down aligners. In the vast majority of cases, the raw material is in sheet form. In other words, aligners are formed from small sections of standard industrial polymeric sheet materials. The materials used are mostly sourced industrially, and they are not necessarily produced specifically for orthodontic aligner application. The commodity-type sheet material is typically manufactured using a continuous extrusion process or a casting process. Sizing of the sheets typically used for suck-down-type appliances can be many feet wide by many feet long, and can range in thicknesses from 0.75 mm (0.030 in.) up to 2 mm (0.079 in.) but thinner and thicker materials are used in special cases.

In order to produce a series of Invisalign-type tooth aligners, an Invisalign technician first scans a patient's upper and lower model set as a means to obtain CAD-manipulatable virtual models of a patient's teeth, gums and soft tissue. A model set normally consists of one upper and one lower plaster model of the teeth, palate and gums. Like Andreiko's methods, such a digital model, once obtained in this manner can be displayed and altered using a software tool known as a computer-aided design (CAD) program. Once the virtual model of the original malocclusion has been obtained, an Invisalign technician will then undertake steps involving extensive manipulation of the virtual malocclusion. This involves extensive repositioning of the teeth according to a comprehensive and sequential procedure, ultimately arriving at a finished or ideal occlusion for that patient. The finished occlusion, even though virtual, is nonetheless consistent with the complete repositioning of the patient's upper and lower occlusion that would result at the end of fully successful conventional orthodontic treatment.

As can be appreciated, after the steps described above are accomplished, an Invisalign technician then possesses two versions of the patient's teeth available within the virtual CAD environment. One version represents the original malocclusion and the other represents the ideal occlusion. In other words, the technician has the beginning and the end states.

It must be noted that the Invisalign technician is not a trained orthodontist. Since the 3D imaging and the corrected case are virtual, they can easily be made available to the patient's doctor online through the internet. Using a special viewing and metrix tool package provided to the doctor online over the internet, the doctor can examine the correctness and precision of the steps taken by the Invisalign technician in full detail. The doctor can approve the work performed by the technician, or provide additional instructions to insure that the actions of the technician are consistent with the doctor's treatment plan for the patient. Ultimately, the doctor must provide his formal approval for the process to continue.

After the attending doctor approves the technician's workup, the next step in the Invisalign process involves the creation of typically 15 to 25 incremental progressive physical forming models. Each of these forming models represents a snapshot of the patient's future occlusion at specific incremental steps along his or her proposed treatment sequence falling between the beginning and the end conditions as described above. To accomplish this, the Invisalign technician creates a virtual "first transition model" that sees a slight repositioning of all or most of the teeth. This first transition model sees some or all of the teeth being subtly moved from their original pre-treatment positions to a virtual first transition position that is in the direction of their intended finished positions. Similarly, a second virtual transition model is created that sees the virtual teeth being moved again slightly further in the desired directions. The objective of the Invisalign technician is to create a series of progressive models, each biased slightly further than the previous one, and each moving the teeth slightly closer to their finished target positions. A final forming model will take the teeth from the series of transition positions and move them into their final, desired positions.

Once such a series of virtual intermediate forming models has been created and a final forming model has been created by the Invisalign technician, the digital code representing each of the models in the series is directed to operate a digital, computer numerically-controlled (CNC) machine known as a rapid prototyping machine. Within a rapid prototyping machine, the series of physical forming models are grown using one of a group of known processes, such as stereo lithography or 3D printing. The growing step results in the production of hard, physical duplicates of each of the series of virtual intermediate models and the final model. These are not virtual models but rather hard, physical models that can be held by hand.

The next step of the Invisalign process sees each of the series of physical models being in turn mounted in a suck-down machine where a combination of pressure, heat and vacuum is used to form the actual series of progressive aligners from plastic sheet material of a constant thickness. Once the series of progressive aligners are formed and trimmed, they are sequentially labeled, packaged and shipped to the attending orthodontist. The orthodontist then schedules an appointment for the patient, at which time the aligners and instructions for their use are given to the patient. The patient will be instructed to begin wearing the first set of aligners for a period of time, typically two weeks. After that, the first set is discarded and the patient transitions to the next set of the series and so on.

The aligners serve to urge the patient's teeth to move according to the positional biases created virtually be the Invisalign technician. The teeth are progressively biased and urged to move in desired directions toward their predetermined finished positions by the resilience of the polymeric material of the aligner. In response to the gentle but continuous forces delivered by the aligners, certain physiological processes involving the creation and resorbtion of the bone supporting the roots of the teeth are initiated. The net result is the slow, progressive orthodontic movement of the roots of the teeth through the underlying bone toward desirable positions and orientations.

The orthodontists role in aligner-based treatment is essentially relegated to that of monitoring the physiological response of the teeth and monitoring the patient's cooperation with the treatment schedule. The attending orthodontist is not required to establish the progressive sequence or otherwise direct the treatment because the functionality of the aligners and the tooth-moving protocol is determined off-site by the Invisalign technician at the orthodontic service center. The orthodontist still must evaluate and approve the work-up provided by the Invisalign program.

As a whole, digital advancements in orthodontics have increased the versatility of the virtual occlusion data and have expedited or eliminated some traditional operatory steps. These trends can involve the introduction of new equipment and software into the orthodontic practice that has not been considered as standard dental laboratory equipment in the past. For example, doctors must acquire and become familiar with 3D analytical software, which is included with the Invisalign program in order to view the virtual occlusion created by an Invisalign technician as described earlier. Another example is CAT scanning equipment optimized for use in dental operatories, which is becoming commercially available for in-office installation. Similarly, acquisition of in-office scanning equipment and rapid prototyping equipment would move some of the Invisalign process steps from the commercial service center directly to the "back room" laboratory of an orthodontic practice. These are all aspects of what some refer to as the emerging "digital orthodontics."

However, the large capital expenditures and technical sophistication required for existing digital orthodontic systems, such as the Invisalign program, have required the use of a central facility to produce aligners. This tends to increase costs and introduces an element of delay in meeting the needs of patients.

The conventional suck-down techniques of the type produced through the Invisalign program also limit the types of aligners that can be formed. Ideally, a thin sheet of polymeric material is used to form an aligner having an approximately constant wall thickness. In fact, vacu-forming often results in regions in the aligner having reduced or uneven wall thicknesses, which can be undesirable. Also, it is sometimes desirable to selectively create a thicker aligner wall adjacent to specific teeth (e.g., molars or an especially mal-positioned tooth) to exert greater corrective forces. This is very difficult or impossible to accomplish with conventional suck-down forming techniques.

Solution to the Problem

Extending the emerging trends in digital orthodontics, the present invention enables all of the hardware and software needed for many of the Invisalign-type processes to reside in a doctor's office or more practically, in a multi-doctor dental clinic where the capital investment for such capabilities can be shared. In particular, the present invention eliminates the necessity for the rapid prototype-produced forming pattern portion of the Invisalign process described above. It involves the introduction of a bench-top CNC milling machine as a piece of equipment that can be used and maintained on-site within a typical orthodontic practice. The combined use of CAD/CAM software and a CNC milling machine provides a fully automated means for directly machining orthodontic aligners. This eliminates the need to grow patterns for aligners by means such as laser lithography, which typically requires a large central facility.

In contrast to vacu-forming a thin sheet of material as is required for the conventional suck-down process, the present invention employs CNC machining of a solid block of material. This approach allows greater flexibility in producing aligners with variable wall thicknesses to customize the forces exerted on specific teeth or an individual tooth, and also in accommodating aligner auxiliaries, such as tacks, bumps, and windows.

SUMMARY OF THE INVENTION

This invention provides a system for producing orthodontic aligners by CNC machining. A digital model of the patient's dental anatomy is manipulated using CAD software to create a solid CAD model of an aligner. A CNC milling machine is then used to machine the inside and outside surfaces of the aligner from a block of suitable material. A progressive series of aligners can also be designed.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
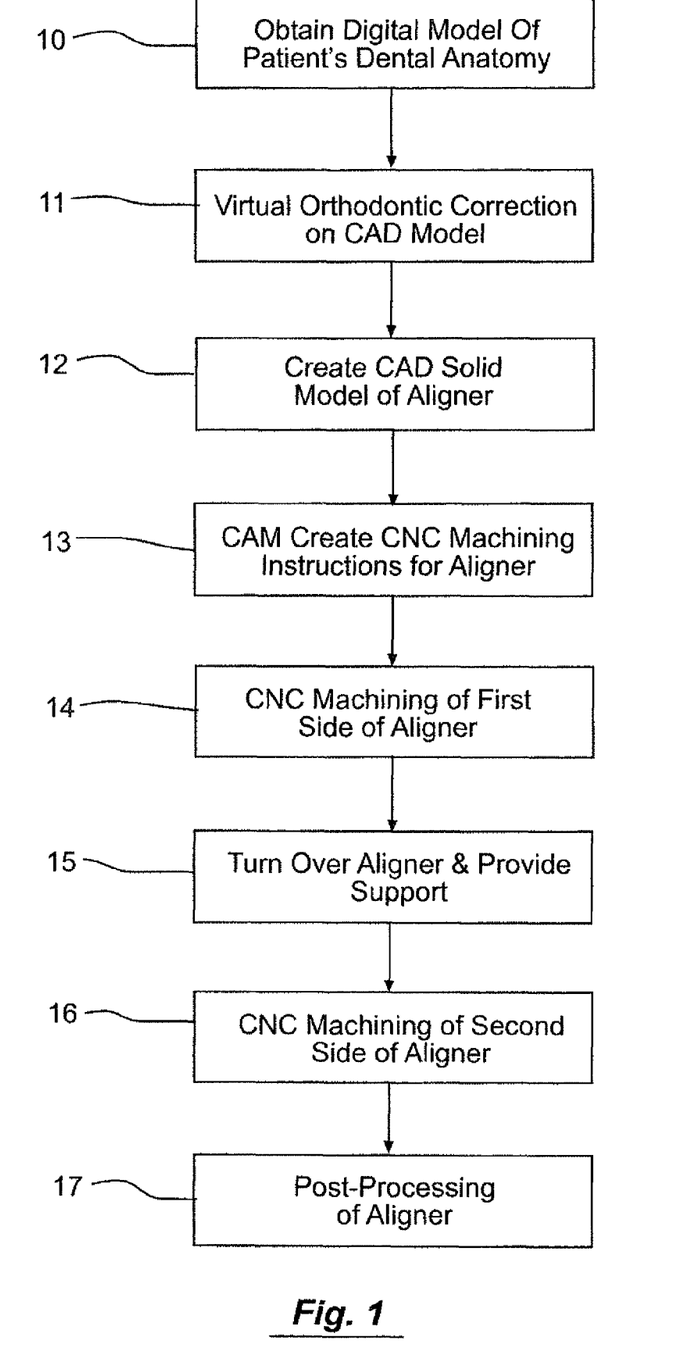
FIG. 1 is a chart depicting a sequence of steps for processing a case according to the present invention to produce aligners for an orthodontic patient.
Figure 2:
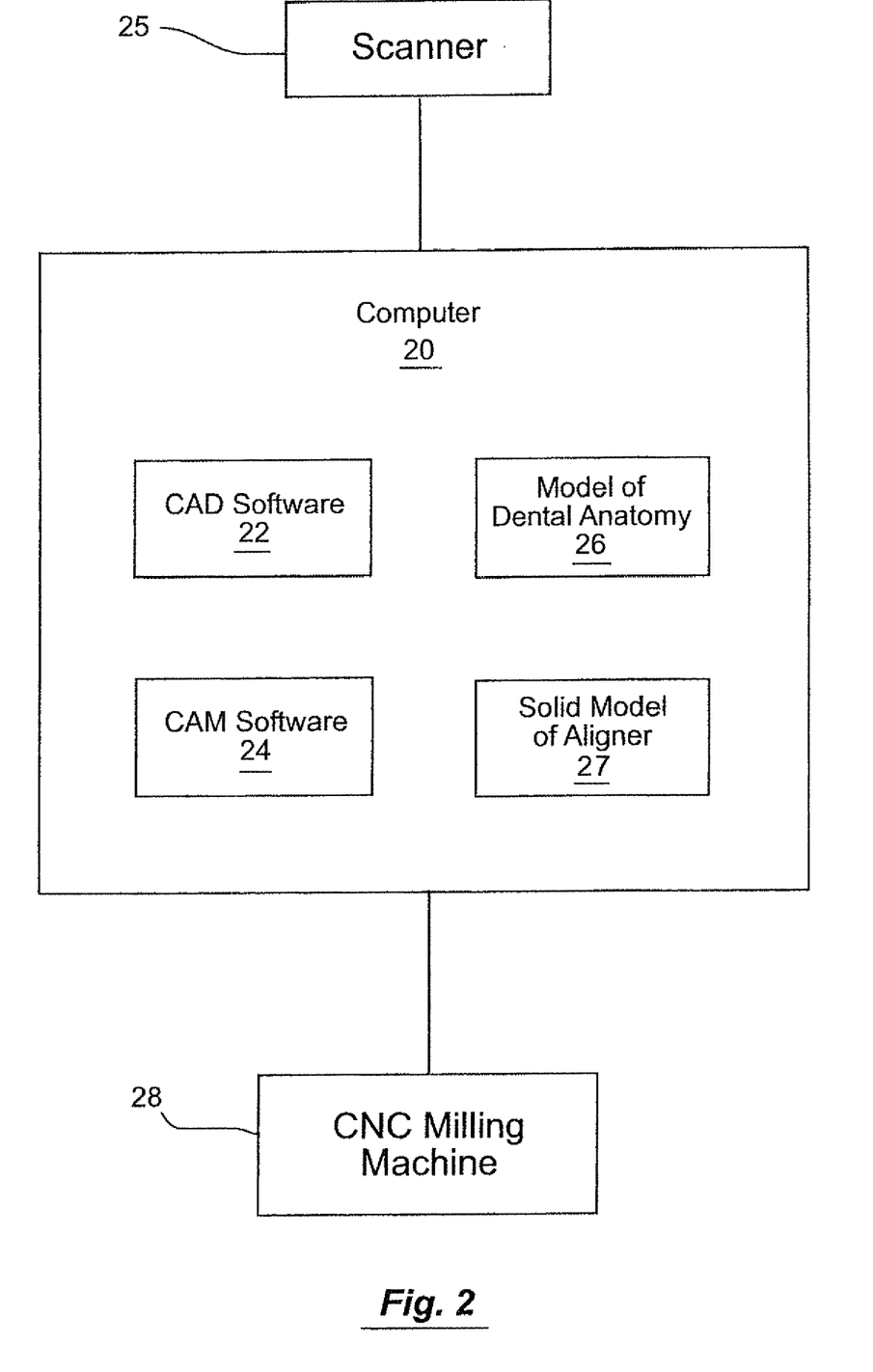
FIG. 2 is a block diagram depicting the major system elements used to form aligners according to the present invention.

Turning to FIG. 1, a flowchart is provided depicting a sequence of steps for processing a case according to the present invention to produce aligners for an orthodontic patient. FIG. 2 is a block diagram depicting the major system elements of the present invention. As an initial step 10 in FIG. 1, a digital model of the patient's dental anatomy must be scanned 25 to serve as the beginning state for orthodontic treatment. This can be done in any of a variety of ways, including scanning a stone model or dental impressions, or directly scanning the patient's dental anatomy with an handheld optical scanner or CAT scanning a negative impression of the teeth.

As indicated in FIG. 2, this data is entered into a computer 20 so that it can be viewed and manipulated with CAD software 22 in the form of a CAD model of the patient's dental anatomy 26. The CAD technician can then interactively modify this model of the patient's dental anatomy 26 via the CAD software 22 to provide virtual orthodontic correction (step 11 in FIG. 1). For example, this can be a process similar to the Invisalign program outlined above for making a progressive series of virtual orthodontic corrections to the model that are later used to generate a progressive series of orthodontic aligners used over the course of treatment. In a simpler case, the user can make virtual orthodontic corrections to a single tooth or a set of teeth in the CAD model to be implemented by a single aligner. The number of modified CAD models (i.e., the number of aligners to be fabricated) and the virtual orthodontic corrections incorporated into each model are subject to the discretion of the technician and subject to the assumptions regarding the degree of physiological response that can be elicited from one aligner.

In step 12 of FIG. 1, each modified CAD model is used to create a CAD solid model of a corresponding aligner. The reader should understand that an aligner and its corresponding forming pattern (e.g., as used in the Invisalign program to form an aligner) are nearly identical in terms of the CAD surfaces that define them. In other words, when holding an aligner in one hand and the pattern from which it was sucked down in the other, each hand represents two embodiments of essentially the same virtual CAD model (i.e., negative and positive representations of each other). To further illustrate the nature of these similarities, the reader is asked to note that the generally convex exterior surfaces of an Invisalign-type suck-down forming pattern are identical in a 3D topological-sense to the internal, generally concave surfaces of the corresponding aligner that would be formed from that pattern.

For defining the exterior surfaces of an aligner for the purposes of robotically machining those surfaces, a standard capability of 3D CAD software 22 called the "offset surface" function can be employed by a CAD technician. Using this function, a slightly outwardly-expanded second surface can be defined, which is in a sense concentric with the original inner surface 42. Such a surface may be used to drive a CNC machine 28 for machining the outer surface of an aligner. Alternatively, a slightly inset set of surfaces can be obtained by uniformly offsetting the pre-established features inward from the originally defined surfaces. In other words, a thin-walled polymeric aligner can be viewed as opposing first and second sides offset by a predetermined range of thicknesses.

In order to fully define a CNC-machined aligner, a CAD technician may instruct the CAD software 22 to create a surface that is offset at all points at a distance of 1 mm for example from the predefined surface derived from the patient's virtual occlusion. It should be pointed out that the CAD software 22 will treat any space created between the original inner and the offset outer surfaces as solid material and not just empty space sandwiched in between the inner and outer surfaces. For example, after defining the periphery of the aligner and virtually trimming it, a completed virtual aligner 27 with a uniform thickness (e.g., about 1 mm) will reside in the virtual CAD space.

Figure 3:
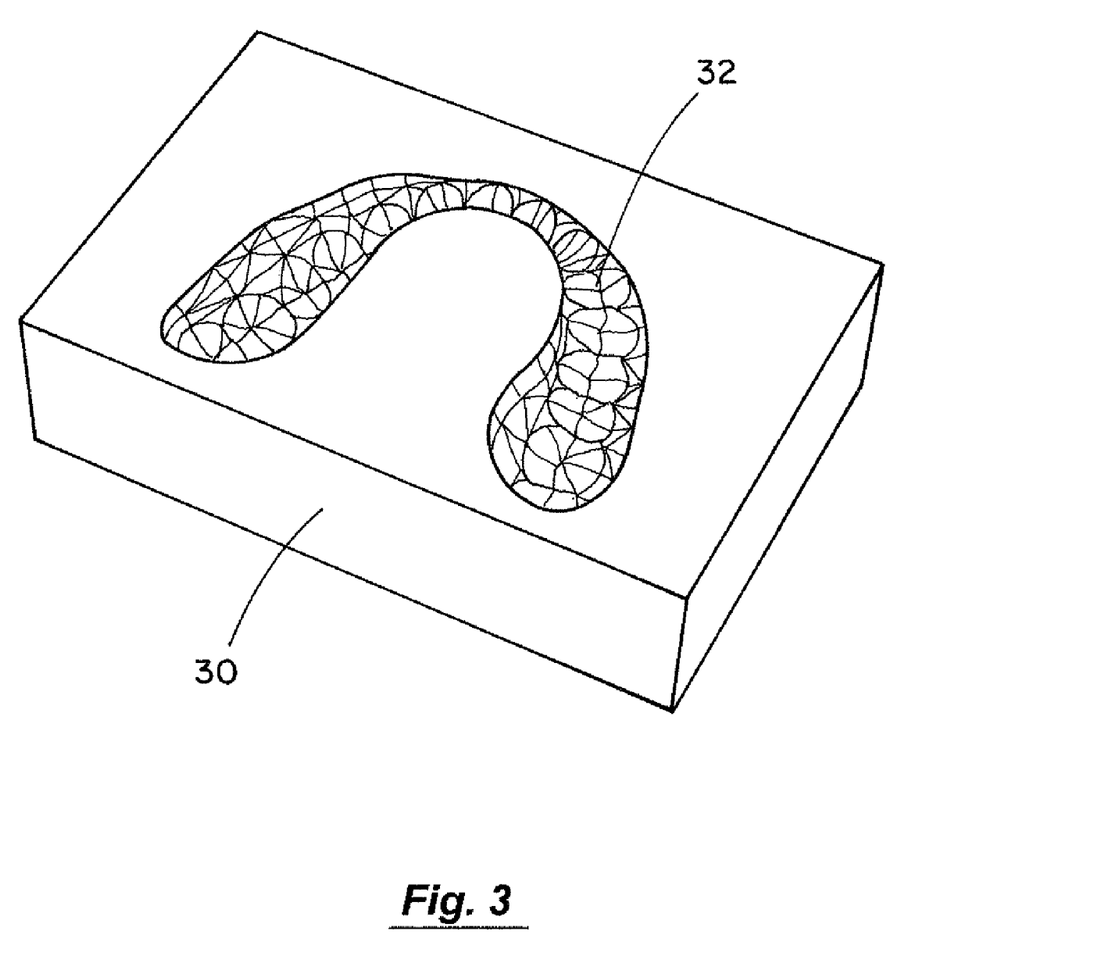
FIG. 3 is a representation of a CAD model 30 for creating one surface of an aligner from a negative 32 of the patient's teeth.

As can be appreciated then, the virtual creation of aligners is based on similar steps to those used in the Invisalign process for defining and creating the patient's virtual occlusion. Importantly though, an aligner can be designed directly from the virtual models of the dentition 10 essentially by allowing that virtual model to define the inner surface of an aligner. For example, FIG. 3 is a representation of a CAD model 30 for creating the inner surface 32 of an aligner from a negative of the patient's teeth. Once defined, the outselling step (offset surface function) described above can be used for producing a second set of those surfaces (i.e., the outside surfaces of the aligner). The outsetting value establishes the default thickness of the aligner.

The present invention then involves machining operations based on the virtually-defined inside surfaces and outer surfaces of the aligner in the CAD solid model 27 of the aligner. It follows that just as the outer surfaces of an Invisalign forming pattern can be robotically created, so can the outer surfaces of an aligner. Further, just as CAD software can define an offset surface, such an offset surface can also be robotically machined. This means then that both the inner 42 and outer surfaces of an aligner can be machined and thus a complete aligner can be machined. Conventional computer-aided manufacturing (CAM) software 24, such as Master-CAM, can be use to convert the surfaces of the CAD model into a series of machine instructions for a CNC milling machine (step 13 in FIG. 1).

Figure 4:
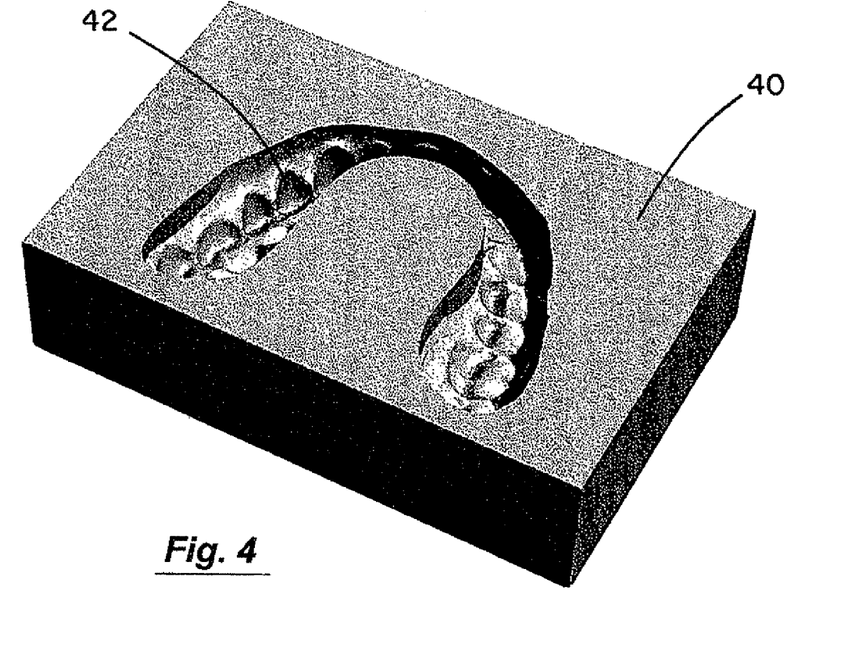
FIG. 4 is a perspective view of a block 40 of raw material in which a negative of the patient's teeth has been CNC-machined using the CAD model 30 shown in FIG. 3 to become the inside surfaces of an aligner when complete.
Figure 5:
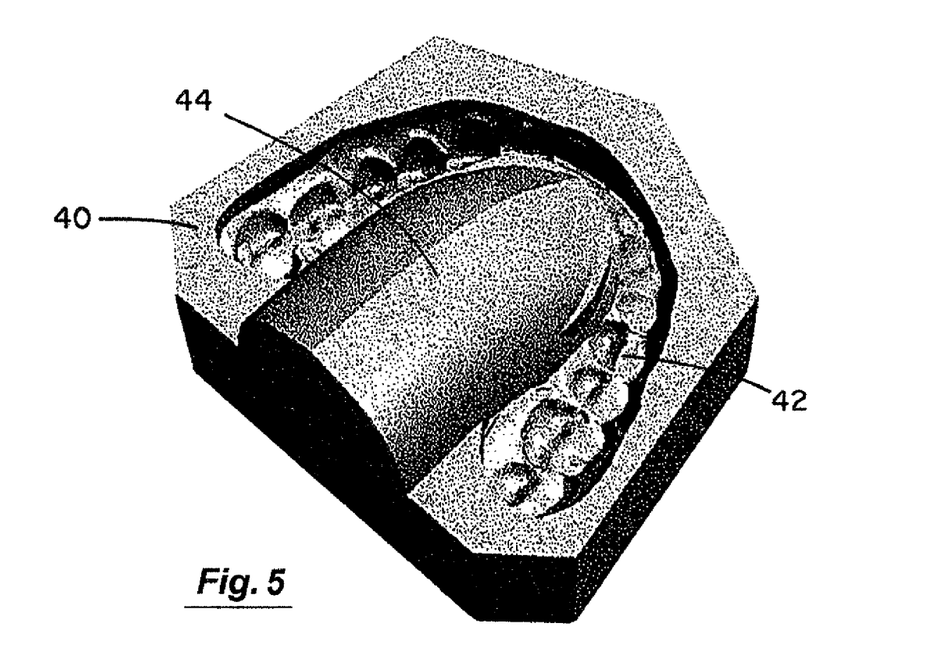
FIG. 5 is a perspective view of a block of raw material 40 in which a negative of the patient's teeth 42 and palate 44 have been CNC-machined to become the inside surfaces of an aligner when complete.

A lightweight CNC milling machines, such as the MDX-40 milling machine or others models offered by Roland Inc. (Roland ASD, 25691 Atlantic Ocean Drive, B-7, Lake Forest, Calif. 92630) is suitable for the purposes of this invention, and would be a reasonable addition to the laboratory-type dental equipment commonly found in orthodontic practices. For machining an aligner, an appropriately sized block of suitable material 40 (i.e., a blank) is mounted on the platen of a CNC milling machine 28 and registered relative to the orthogonal coordinates of the machine. For example, the blank can be a block of a suitable polymeric material. The blank can be generally U-shaped block of material roughly approximating the patient's dental arch to reduce machining. The bulk of the material can be machined away within the CNC milling machine 28 using large cutting tools and appropriate spindle RPM and feed rates for maximum material removal. The inside surfaces 42 of the emerging aligner would be machined first using progressively smaller cutting tools as per programming instructions established within the CAM software 24 for defining aligner features adjacent to interproximal areas, gingival margins and the exact topology of the occlusal anatomy of the teeth (step 14 in FIG. 1). A tool changer portion of a CNC milling machine 28 may be loaded with many such cutters, with the smallest of the series being for example a 0.012 diameter ball mill. Such a cutting tool is well sized for forming fine features and detail of the aligner. FIG. 4 is a perspective view of a block 40 of raw material in which a negative 42 of the patient's teeth has been CNC-machined from the CAD model shown in FIG. 3. The biological surfaces machined into the block 40 become the inside surfaces of the aligner. FIG. 5 is a perspective view of an alternative embodiment of the inside surfaces of an aligner including palatal surfaces 44. The palatal surfaces 44 contact and span the palate transversely when the aligner is complete.

Figure 6:
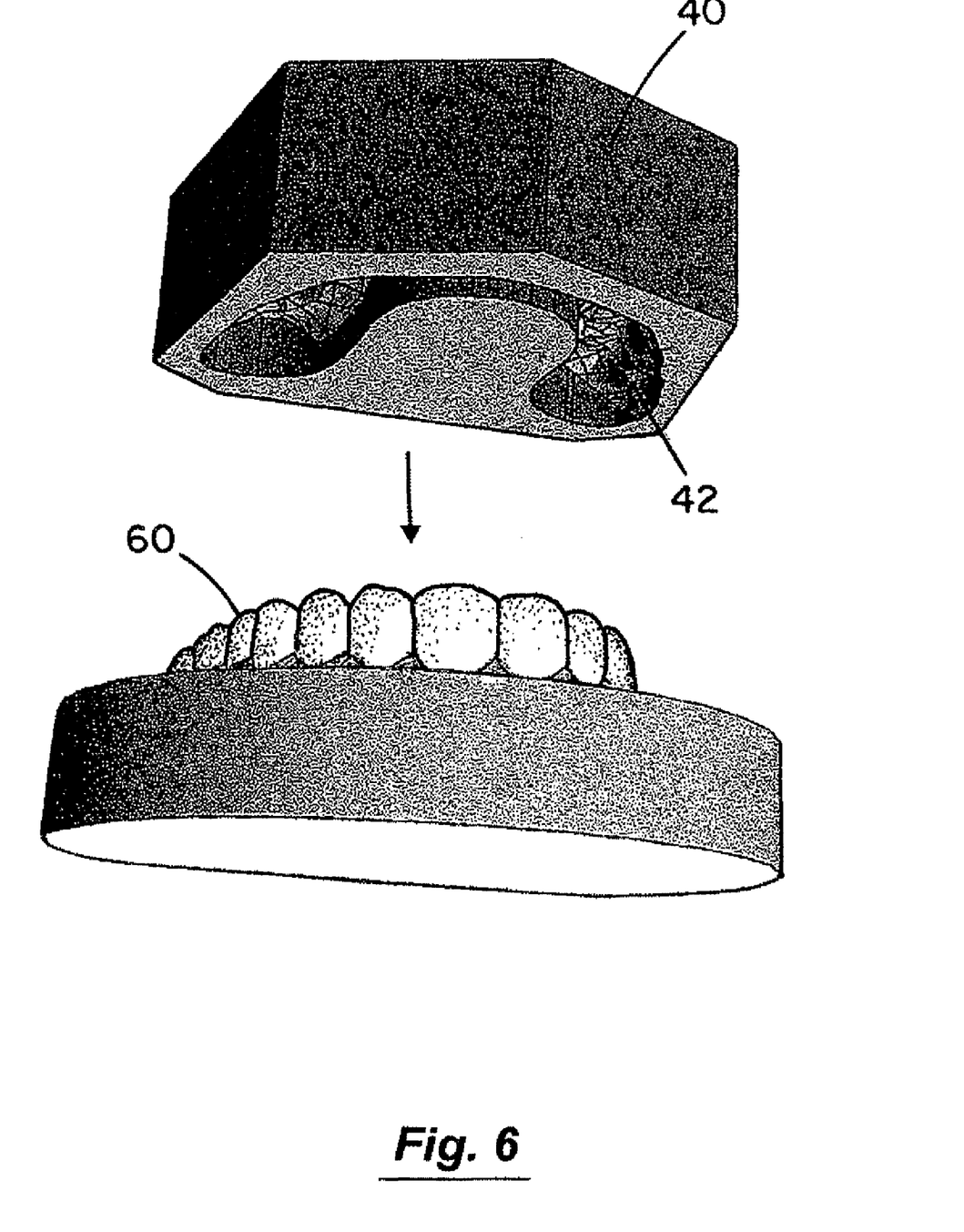
FIG. 6 is a perspective view illustrating a CNC-machined block of material 40 in the process of being positioned on a support 60 prior to machining the outer surface of the aligner.

To accomplish machining of the outer surface after the inner surface 42 has been machined, the material 40 is turned over, orienting the inside surfaces 42 downward. As can be appreciated, at this point the machining of the exterior surfaces of the aligner could cause the material being machined to deflect away from the milling cutters since the material is essentially hollow. To avoid such deflection, the entire block of material 40 from which the aligner is being machined may be supported on a CNC-machined holding pattern 60 formed of any suitable material (step 15 in FIG. 1). For example, the holding pattern 60 can be a positive mirror image of the same negative surface topology as the inside surfaces 42 and as such with the material 40 placed on the holding pattern 60. The pattern 60 would intimately support the inside surfaces 42 from deflecting inward in response to cutting tool forces. FIG. 6 is a perspective view illustrating a CNC-machined block of material 40 being positioned on a holding pattern 60 prior to machining the outer surface of the aligner. The machined block 40, when fully seated and in position on its holding pattern 60 sees all of its generally concave features and surfaces being intimately supported by all of the generally convex features and surfaces of the holding pattern 60.

The holding pattern 60 on which the material 40 rests while the outer surfaces are machined can be designed from the CAD model of the aligner since the surface of the holding pattern 60 can be complementary to the inside surface of the aligner. Thus, the CAD model can be produced by a CNC milling machine using a set of instructions generated based on the CAD model of the aligner. The holding pattern 60 can be machined at a lower resolution and can be machined with larger cutting tools than the aligner itself. This reduces time required to machine the holding pattern 60. Further, the holding pattern 60 need not be machined from the same material from which the aligner is being machined. In fact, it can be machined from a material optimized only for low cost and rapid machining. Alternatively, such a holding pattern 60 may be formed from other forming processes such as a digital process based on forming a part with epoxy and cornstarch, such as with a 310 Plus rapid prototyping machine available through Z Corp. of Burlington, Mass. As yet another alternative, the holding pattern 60 may be produced by casting in materials such as stone or rigid foam produced by digital means. In addition, the holding pattern 60 can be more efficiently formed to support only selected regions of the aligner (e.g., only the thinnest regions of the aligner).

After the material 40 has been turned over and supported by the holding pattern 60, the outer surfaces (i.e., second side) of the aligner can be machined by the CNC milling machine (step 16 in FIG. 1). It should be understood that the order of machining the surfaces of the aligner can be reversed (i.e., the outer surfaces of the aligner could be machined before the inner surfaces). Either the inside of the aligner or the outside could be the first side machined by the CNC milling machine, with the opposing surface constituting the second side to be machined by the CNC milling machine.

Figure 7:
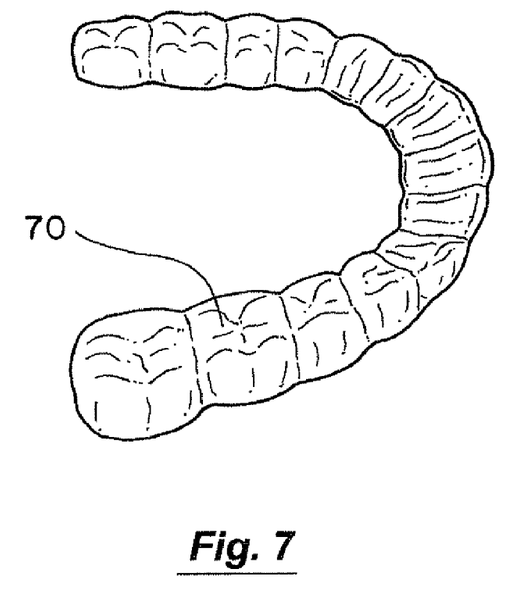
FIG. 7. is a perspective view of a finished aligner 70 fabricated by machining according to the present invention.

The present invention anticipates that the step of trimming away excess material and the contour trimming of the gingival edge of an aligner can be yet another step to be defined preferably at the CAD design stage or the CAM programming stage. Alternatively, a manual trimming operation can be used. Other post-processing steps (step 17 in FIG. 1) can also be performed as needed. In any event, a fully machined and complete aligner 70 results, as shown in FIG. 7.

One drawback of the CNC-based machining process is that the resulting finish of the surfaces of a CNC-machined aligner 70 may fall short of the generally transparent optical clarity of a conventionally-produced aligner using the suck-down process. The finish of both the internal and external surfaces of a machined aligner can be improved through specifying the smallest permissible scallop height and the use of larger ball end mills and higher spindle speeds during the CAM-programming stage. Such steps for improving finish are well known within the CAD/CAM machining field.

Machined aligners 70 may be post-process polished for higher clarity using flame treating, or chemical treatments or tumbling in certain types of soft media such as corncob and wood chips. Regarding processes for improving the finish of an aligner that involve flame treating, flame treating may tend to cause slight shrinkage of the otherwise completed aligner 70. To avoid shrinkage, flame treating may be accomplished while the aligner 70 is positioned on its corresponding support pattern 60.

One benefit of the CNC machining process for creating aligners is that the cost, time and waste involved in creating an intermediate forming pattern, and the subsequent suck-down step are eliminated. Further, as described, the suck-down process for forming aligners involves heat, very similar to the industrial process known as vacu-forming. It is well known that the vacu-forming of plastics in sheet form tends to cause the plastic being formed to shrink and draw-up due to heating. The present invention does not involve such heat forming and therefore the issues of sizing, shrinkage and distortion are bypassed, as well as the necessity of slight scaling operations to compensate for shrinkage at the virtual CAD level. In addition to these benefits, other important advantages associated with fully-machined aligners become realizable through such a process and are described below.

The present inventor has developed considerable experience in the use of aligners for orthodontic treatment and has brought forth other improvements. For example, U.S. Pat. No. 6,293,790, "Heated Orthodontic Pliers" to the present inventor discloses a series of steel dental pliers useful for modifying polymeric shell aligners. They are available commercially and are known as Thermopliers™. The Thermoplier family is a group of hand-held steel instruments that in use are heated to a predetermined temperature. Once heated, they are directed to an aligner to effect local heat-softening and thermal flowing (or thermoforming) of the aligner structure thereby forming various types of useful features and alterations. An example of the use of Thermopliers to augment aligner-based therapy follows:

One representative application demonstrating the use of Thermopliers involves a technique that addresses a common problem faced by orthodontists. The problem is the difficulty encountered in correcting undesirably rotated teeth. Unfortunately, the slight positional bias or slight out-of-register relationship between an aligner's tooth-receiving compartment and its corresponding tooth will produce force vectors that are not well-suited for correcting undesirably rotated teeth. Rotations, in contrast to torqueing and tipping-type corrective forces, are more difficult to deliver using aligners. To augment an aligner's capability to fully correct a rotation, orthodontists use one of the set of Thermopliers configured to thermoform a small, sharp, inward-facing bump in the structure of the aligner. Such a thermoformed bump requires skillful manipulation of the pliers to form a bump positioned in the wall of a tooth-receiving compartment of an aligner. When such a modified aligner is seated in position in the mouth, the location of the bump is such that it produces a force vector of maximum mechanical advantage to desirably rotate the tooth.

To illustrate the use of such bumps in treatment, consider a disto-lingually rotated maxillary lateral left tooth for example. A first bump may be placed at the disto-incisal position to contact the tooth on its disto-lingual surface, and a second bump may be formed at the mesio-labial, incisal location of the same compartment. During treatment, such a pair of co-working bumps cooperate to create a coupled rotational force in a mesial-lingual direction according to this example. Such balanced, coupled forces have proven to be very effective in accomplishing rotational corrections using aligners. Continuing with this example, a practitioner may first achieve partial rotational correction through the use of a plain, as-formed aligner devoid of any such alterations, relying only on the positional biases of the aligner's compartments to accomplish a portion of the needed rotational correction. After the teeth have responded over time to the as-is aligner, the remaining correction needed to fully correct a rotated tooth can be achieved by activating the aligner through using the appropriate Thermoplier as described. To fully exploit the corrective capacity of an individual aligner, the thermo-formed activation bumps may later be thermo-formed a second time so as to extend even further into the tooth-receiving compartment. In this manner, a single aligner can serve for multiple progressive treatment phases before being spent and discarded. Progressive activation in this manner serves to counter force level reduction resulting from the dissipation of corrective forces as the teeth respond and move. Such revisions also serve to maintain more constant biological forces on the teeth being repositioned, which is generally thought to promote the most rapid tooth movement.

Bumps as described serve to focus energy stored locally in the region of the aligner's structure adjacent to a bump. The inward-projecting bump causes an outward flexing of the aligner material in a region away from the tooth surface. Configured in this way, bumps gather stored energy from a wider area and impinge that energy onto the tooth at the most mechanically advantageous point, thus focusing corrective forces most efficiently.

Figure 8:
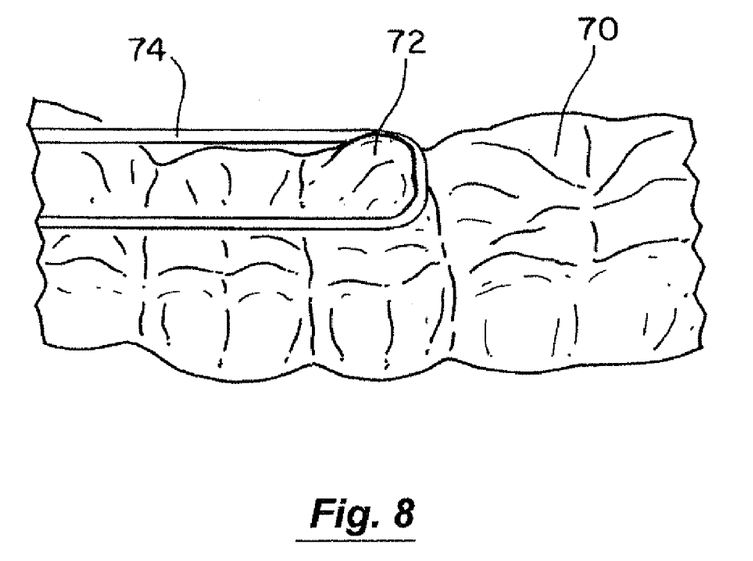
FIG. 8 is a detail view of a portion of an aligner 70 showing an area 72 that is machined allowing thicker material to accept an elastic 74.

Another of the Thermoplier family of instruments has features formed in its beaks that serve to thermoform an elastic hook feature directly in an otherwise featureless area of an aligner's structure. Elastic hooks 72 are used as anchor points for orthodontic elastics 74, as depicted in FIG. 8. Elastics 74 provide tractive forces between sectioned portions of an aligner 70 (or an aligner and other structures fixedly attached to the teeth) as needed during treatment. Similarly, other Thermopliers are used to enhance the performance of aligners by installing other thermo-formed features in the polymeric shell.

Another practice used by orthodontists that involves altering a polymeric shell-type aligner beyond its original as-formed configuration should be considered. The reader is asked to consider the interior, tooth-contacting surfaces of each of the series of tooth-accommodating compartments formed in an aligner. As can be appreciated, the inside surface of any one compartment completely surrounds and is in intimate contact with its tooth when the appliance is seated and in position. In order for forces such as those that are created through the installation of a single bump to be effective in moving the tooth, the interior wall on the opposite side of the compartment must be relieved or removed to permit the tooth to move in that direction. In other words, an axiom for orthodontically moving teeth could state that if a force is applied to move a tooth in a certain desired direction, the tooth will not move in that direction unless all obstacles have been cleared and free space is provided for that tooth to move into. To handle such situations, orthodontists may alter aligners by discretely cuffing away material to create such needed free space. Such features are referred to as "windows". Windows are created by trimming away aligner material in the direction of desired tooth movement. A window in an aligner will be created for example on the labial side of a tooth if the treatment plan requires that a bump be formed on the lingual side. This allows the focused force exerted on the lingual side of the tooth by the bump to avoid an equal but opposite restrictive force on the labial, and thus the tooth will in fact move labially into the open window cut out of the aligner on its labial side. Another means for creating free space is to use another one of the family of Thermopliers. When heated, the particular Thermoplier can be used to work the aligner material on the labial side of a tooth, still referring to the example above. In effect, a bubble can be formed as an outward extending feature of an aligner. When shaped correctly, the space can allow a tooth to move into that free space, but at the same time, provide a stop for the tooth, preventing it from moving further than desired and all the while sheltering the tooth from the gentle but unwanted inward forces of the lips and cheeks.

Another example of the installation of useful thermo-formed alterations installed in an aligner's structure involves this: In order to tip a tooth inward or outward (known as correction in terms of torque) but considering a case where that the tooth is essentially in its proper position and only requires up-righting (torqueing) to its desired orientation, a window can be cut into an aligner in an area limited to the incisal half of the tooth. With the installation of a bump near the incisal edge on the lingual side, the incisal edges of the crown will slowly respond by swinging into the relief of the window on the labial. Since in this example, the bulk of the aligner compartment still holds the more gingival portions of the crown stationary, the tooth will be up-righted without any bodily displacement away from its desired position.

In this general manner then using these and similar methods, orthodontists can create pushing forces on one side of a compartment and discretely relieve the opposite side to very accurately tip, torque, rotate and bodily move the roots of teeth through the supporting alveolar bone. As can be appreciated, aligner-based therapy has to a large degree grown into a full treatment modality, no longer limited to minor tooth movement, minor correction or finishing functions.

Other methods for exploiting the full treatment potential of polymeric shell aligners are currently being mastered by orthodontists and circulated within the orthodontic literature. Along with the use of Thermopliers, the relieving of aligners by the creation of windows and the like, and other means for amplifying, regulating, reactivating and extending the corrective force-generating capability of aligners are becoming known. For example, the Applicant's U.S. Pat. No. 6,702,575, entitled "Orthodontic Aligner Auxiliary System", teaches other techniques for extending the usefulness of aligners and is hereby incorporated by reference. The '575 patent involves the installation of separate auxiliary devices into the physical structure of aligners and related methods for preparing aligners to accept and retain such devices. To follow is a description of these devices, along with descriptions of how they function and the preparatory steps that must first be taken so that such devices can be installed into an aligner's structure.

The '575 patent involves the introduction of a group of small devices that are intended to be strategically positioned and attached to an aligner's structure. Such devices are termed "aligner auxiliaries." Prior to installing such devices, a doctor may assess the progress of a case at mid-treatment for example and in particular, make note of problem areas where the desired tooth response is lagging or instances where particular teeth are stubbornly not moving in response to treatment forces. Aligner auxiliaries are installed in those locations to amplify and focus corrective forces of the aligner to enhance correction. For example, an auxiliary known as a tack 90 (see FIG. 9) can be installed after a hole of a predetermined diameter is pierced through a wall of a tooth-containing compartment of an aligner. The diameter of the hole is slightly less than the diameter of a shank portion of the tack. Next, a tack-installing plier is used to forcibly pop the retentive head of the tack 90 through the hole, resulting in the tight and secure retention of the tack within the aligner structure. The tack pops into position where it is tightly retained in the aligner within the punched hole. Such progressively-sized tacks and other auxiliary devices are commercially available to orthodontists who use them to augment and extend the tooth position correcting forces of aligners.

Figure 9:
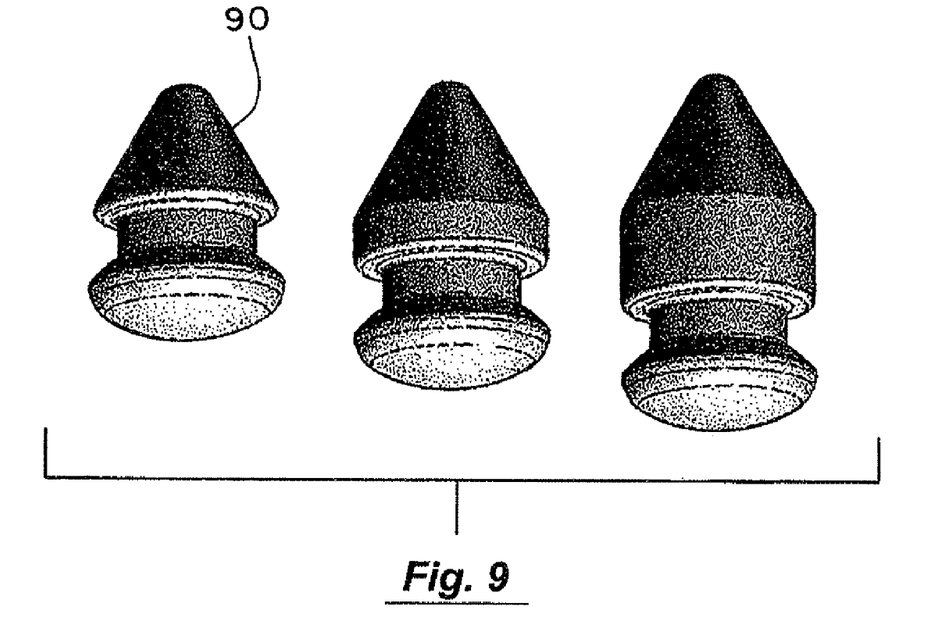
FIG. 9 is a perspective view of a series of progressive aligner auxiliaries 90 referred to as tacks.

As can be appreciated, the installation of an auxiliary device such as a tack 90 to achieve the delivery of optimal physiological tooth-moving forces is similar to the effect achieved by installing the bump described earlier. The use of a separate tack however permits the forces delivered to a tooth to be progressively regulated over time by using a sequential series of progressively longer tacks as shown in FIG. 9 and described in the '575 patent. In practice, a doctor may adopt a sequential plan where an aligner is first used as-is, without any Thermoplier-type activations, windows, tacks or bumps or any similar activations or additions whatsoever. Such an aligner may be worn by a patient for two to six weeks, but typically two to three weeks. At the next scheduled office appointment, the shortest tack (in terms of labial-lingual extent) would be installed in the aligner. The domed portion would extend into a tooth compartment of the aligner as determined by the clinician. The tack(s) 90 would directly contact and direct force onto their respective teeth. The time period between a patient's appointments is typically adjusted to correspond to an anticipated amount of tooth movement. So at the next appointment, the doctor may remove the shortest tack and install a medium-length tack and the short tack is discarded. As the energy stored in the aligner's structure adjacent to the tack is spent through physiological response of the tooth, the longest of three tacks, can be installed after the medium tack is spent, removed and discarded. The inventor anticipates that with the appropriate instruments, patients may be able to install progressive aligner auxiliaries at home according to a doctor's instructions. Such flexibility would thereby reduce the frequency and cost associated with more frequent appointments and thereby reduce the overall cost of treatment.

The reader should understand that orthodontists have taken advantage of the availability of plain progressive aligners, where only the positionally-biased tooth receiving compartments provide the physiologically active tooth moving mechanism. Invisalign represents one commercially-successful digitally-driven service bureau-type option offering plain progressive aligners to orthodontists. Treatment based on such a progressive series of aligners has proven to be successful, but there is ample need for improvement in several areas. Invisalign-type treatment in extreme cases can require as many as fifty sets of aligners. Even for cases where such treatment involves a smaller number of aligners, it is still by all measures expensive. From the detailed description provided above covering the rich art of aligner augmenting auxiliary features and auxiliary devices that are used to enhance, amplify, focus and extend the force delivery capabilities of aligners, it should be obvious that the affectivity of plain aligners falls short of the full potential of aligners and aligner-based treatment.

In particular, the present invention, which introduces the direct, robotic machining of aligners from a solid blank of material 40 opens the door for simultaneously achieving many features of the aligner-enhancing art covered above. For example, step 11 (virtual orthodontic correction of the CAD model) and step 12 (creation of a CAD solid model of the aligner) in FIG. 1 can be expanded to incorporate features to accommodate aligner auxiliaries, holes, bumps, windows, raised lands, regions of increased or decreased thickness, etc. to be formed in the aligner by CNC machining. The CAD solid model of the aligner 27 can also be modified to incorporate structural attachment points for other orthodontic components to provide inter-maxillary forces or extra-oral forces in orthodontic treatment.

The following is a review of some of the important advantages and the flexibility afforded by the methods of the present invention. An otherwise conventional aligner may be machined using a CNC milling machine 28. Such an aligner can exhibit an outer topology that is offset from its inner topology 42 by a default set thickness, with the thickness value typically ranging from about 0.75 mm to about 2 mm. A uniform thickness will be found at all points throughout the aligner's structure. In comparing a machined aligner to a conventionally vacu-formed aligner, it should be noted that an inherent problem related to the vacu-forming process is that plastic sheet material will thin out in areas of high convexity. In other words, due to the fact that convex features of a vacu-forming pattern tend to absorb more radiant energy during heating, and since the material forming over these hotter convex features sees higher lateral tensile forces as a vacuum or over-pressure is applied, the material will stretch in a laminar manner (delaminate) resulting in decreased thickness at those points. Further, portions of a suck-down aligner located in concave areas such as interproximal troughs and fissures in occlusal molar anatomy will not thin out and may gain measurable thickness. If an aligner is conventionally vacu-formed from 1 mm material (0.040 in.) material, the material corresponding to the cusp tips may thin out to only 0.026 in. Conversely, material located in concave areas may increase to 0.042 in.

As described above, it is well known that common plastics formed by vacu-forming such as egg-crate-type trays and blister-pack retail packaging will shrink to a smaller size than the vacu-forming dies on which such parts are formed. For this reason, standard vacu-forming dies must have a draft angle of several degrees to allow the part to be removed from the tooling once formed and cooled due to such shrinkage. Similarly, conventionally produced suck-down aligners are not immune to such vacu-forming shrinkage in that the temperatures and materials used are generally the same as those used in some standard industrial vacu-forming applications. Any slight corrective scaling function employed at the virtual level to produce compensating, slightly oversized vacu-forming patterns becomes unnecessary when using a CNC machining process to directly machine an aligner. There is inherently no shrinkage to anticipate and counteract.

Taking the heat shrinkage problem further, it is known that that the degree of heat shrinkage any specific area of an aligner exhibits is a function of material thickness and that thinner areas shrink more than thicker areas. As pointed out above, conventionally-formed aligners exhibit varying thickness and therefore, the heat shrinkage becomes differential and thickness-dependant. These factors combine to predict then that thermo-formed aligners inherently include some distortion and unpredictable positional errors caused by differential shrinking from heat forming. The present CNC-machining approach bypasses these problems altogether. A machined aligner can exhibit a uniform thickness throughout because its processing requires no heat whatsoever or processes that invite distortion.

CNC-machined aligners are based on tool paths compiled into machine code stemming directly from the surfaces of a CAD technician-produced virtual occlusion 26. As such, the steps of creating forming patterns, and the inaccuracies associated with the rapid prototyping process employed to grow forming patterns are avoided along with the associated waste, time and cost. For these several reasons, CNC-machined aligners can be more accurate, less expensive and easier to produce than suck-down aligners.

Since the CNC-machining code 13 for machining an aligner 70 can be sent over the internet, and since it is not unreasonable to expect a small, benchtop CNC milling machine 28 to be installed and maintained in an orthodontic practice, it then becomes a practical matter to consider the entire aligner fabrication step being accomplished on-site by the orthodontist and staff, even if the scanning and virtual CAD steps are performed remotely.

As described, the orthodontically active principles behind progressive aligners involve the progressive positional biasing of the tooth-receiving compartments formed in an aligner, but other means for achieving progressive aligners are known. For example, an entire array of activation options has been described above including local thermoforming with Thermopliers and the installation of progressively longer/harder/larger auxiliaries including tacks 90. These modalities can all achieve the progressive function, allowing aligners to be used for a first phase as-is, then progressively activated for a second and third (or more) phase(s) to maintain physiologically appropriate force levels.

Another known means for obtaining progressive properties from a single aligner configuration is to suck-down an aligner over an identical pattern, but sucking down using progressively thicker material. Given three otherwise identical aligners where the thickness of the sheet material from which they are formed is increased from 0.040 to 0.060 in. and then 0.080 in. for example, those three aligners when used sequentially would demonstrate progressive aligner properties. In other words, the thinnest aligner being used first would accomplish a certain degree of tooth position correction. The thicker aligner formed from the same pattern but from 0.060 in. material would then fit over the teeth. Since some tooth position correction has been previously accomplished, the energy storage of the aligner material in the regions of the tooth-receiving compartments would be only partially loaded, but since the appliance formed from a thicker material, the corrective forces delivered to the teeth would be comparable to the mean force level achieved by the thinner, 0.040 in. material version. So, the 0.060 in. version would produce continued tooth position correction and after being spent, the 0.080 in. version would likewise be only moderately loaded even though it is considerably less resilient and conversely, more rigid than the thinner versions.

As can be appreciated, an approach to CNC-machining progressive aligners of increasing thickness has certain advantages. For example, the rate of incremental increase in thickness as described above would not be dependant on standard thicknesses of sheet plastic available as an industrial commodity. An optimal thickness could be established for the CNC machining process. For example, rather than being limited to the 0.040, 0.060 and 0.080 in. sequence, an orthodontist could choose a sequence such as 0.040, 0.053 and 0.066 in. for an adult patient whose teeth are known to reposition more slowly compared to a rapidly growing adolescent patient.

Given the concept that an aligner formed from thinner material generates generally lower corrective forces than an identically configured aligner formed from thicker material, it follows that an aligner could be CNC-machined so as to be thicker in areas where higher forces are needed and thinner in areas where lighter forces are needed. Having the latitude to produce aligners with first a default thickness and then areas of variable thickness could be favorably exploited to help orthodontists address many difficult day-to-day challenges. For example, any malocclusion will consist of teeth that are further from their desired finished positions than other teeth. Further, some teeth are smaller than others of course, and the size of the tooth corresponds to the absolute force threshold needed to initiate tooth movement. Other teeth may seem to be more stubborn due to many factors including the proximity of the tooth's root to the boundaries between cortical and alveolar bony support. Still other teeth are simply harder to correctively rotate, angulate or up-right than others. Still other teeth and groups of teeth may need to be bodily moved as rapidly as possible over comparatively large spans to close open spaces. For all of these reasons, the option of tailoring aligner thickness and thus force levels around regions containing larger teeth or teeth that are further from their desired destinations, or those stubborn teeth allows those selected teeth to receive higher forces than small, nearly ideally positioned teeth.

Historically speaking, one philosophy of orthodontic treatment, known as "Differential Force" called out for the corrective forces directed to teeth to be closely tailored according to the ideal force level requirements of each tooth. The Differential Force philosophy was supported by hardware based on calibrated springs intended to provide only those ideal force levels required. Carrying the concepts of the Differential Force philosophy forward to the precepts of aligner fabrication today, one can appreciate that CNC-machined aligners exhibiting carefully controlled variable thickness according to the present invention can accomplish the Differential Force objectives on a tooth-by-tooth basis. The compartments surrounding teeth can have wall thicknesses established at the CAD/CAM level by a technician based on the needs of each tooth. A CNC-machined aligner can have a limitless series of regions, each with a unique offset thickness between its inner and outer surfaces.

Another important benefit attainable only through the CNC machining of aligners is the versatility or design freedom to prepare an aligner for receiving the group of aligner activations and aligner auxiliary devices, which were described earlier. A representative example of how CNC machining can facilitate or accommodate such additions to aligners is by mimicking the function of one of the current inventor's commercialized Thermo-pliers, which was also described above. The particular Thermo-plier exhibited features that when heated and directed to an aligner were capable of thermo-forming a hook structure directly into the aligner structure. Such a structure 72 serves as a stanchion for attaching elastics 74. Elastics used in orthodontics span a wide range of wall thicknesses and diameters and in some cases elastics can generate a considerable tractive force of several hundred of grams. In cases where those high tractive forces are called for, it would be beneficial for the region of the aligner selected for receiving the thermoformed hook 72 to be reinforced in order to be more capable of withstanding potentially destructive or distortion-inducing forces. Thickening the hook-receiving region 72 provides exactly that type of reinforcement so that a hook formed in a thickened region is stronger and stiffer and thus better able to handle heavier elastic forces without distortion of the adjacent area. In addition, CNC machining could be used to form hooks 72 and similar features in an aligner.

Another example of the use of the inventor's pliers described earlier related to installing tooth-contacting bumps. A particularly difficult rotation such as correcting a mal-rotated maxillary central tooth may call for an extra energetic, extra-robust bump capable of delivering higher forces than are typically required. In such a situation, only the area to receive the larger than normal bump would be identified at the virtual modeling level as an area to be machined thicker than the surrounding material. During the CNC milling step, the offset distance (the thickness between the inner and outer surfaces) would be specified at a larger value for the area surrounding a bump feature. For example, the overall default thickness of the aligner may be 0.035 in., but the region to receive an extra energetic bump may be increased to 0.042 in. Yet another example of the benefits of CNC machining aligners according to the present invention rather than thermo-forming involves the step of installing a window-type relief in an aligner. Such an area would simply be machined away from the inner surface 42 to create a window.

To provide yet another example; generally speaking, aligners are not considered to be well suited for orthodontic cases involving significant orthopedic discrepancies. Deep bites, open bites, narrow arches, and narrow, vaulted palates are examples of such discrepancies. Other problems such as molar relationship discrepancies are also considered orthopedic problems involving out-of-ideal relationship between the two arches. Normally, to apply corrective forces required to address such larger orthopedic problems, extra-oral anchorage is sometimes required. Orthopedic correction can also call for the gathering of one entire arch to serve as an anchorage abutment against the other arch. Conventionally-formed aligners, being formed from relatively thin sheet plastic material do not have the structural integrity to provide such highly loaded anchor points. After all, even slight distortion in an aligner's structure alters the position of the tooth-receiving compartments, which impacts tooth moving vectors. Being uniformly thin, conventional aligners react with significant distortion if subjected to heavy external loading and such forces may unseat a conventionally-formed aligner from the teeth altogether. The present invention however allows for significant thickening and reinforcement in areas subjected to such high forces. For example, portions of the aligner's outer surface need not always be maintained in concentric relation with the inner surfaces of an aligner, particularly in the posterior region. CAD-creation and CNC-machining of an aligner permit the exterior surfaces of an aligner to be oriented or configured independent of the inner surfaces. This allows full design freedom for providing orthogonally configured attachment points. The aligner structure can be thickened considerably. Thicknesses of sufficient depth for female threads to be installed for an attaching screw become possible. As such, those portions can be far stiffer than the thinner buccal segment and anterior portions. For example, at certain cross section locations, the posterior ends of an aligner may be as much as 6 mm (0.236 in.) or nearly ¼ inch thick. Such reinforcement provides ample structural rigidity for high force levels associated with orthopedic corrections and extraction site closure for example.

Conventional thermo-formed aligners, being thin and uniformly flexible are never configured to transversely span the palate as do well known devices such as rigid acrylic devices like retainers. Any palate-complying structure comprising thin, conventionally formed aligner material would likely itself distort and fail, but in any case, such thin structures would not be capable of sustaining, transferring or resisting any forces by transferring them to the palate. Aligners of the present invention however could very well have palate-contacting features 44 extending from the lingual-gingival margin up and over the palate transversely. Such palatal-compliant portions could be machined with thicknesses ranging from 2 to 4 mm. Lower aligners can similarly have structure that intimately rests on soft tissues of the mandible. Such upper and lower features can be machined with relief to accept palatal expansion devices, transpalatal springs and the like or features that serve in what is called the Nance position. Another set of structures consisting of relatively sharp points and ridges can be machined into the anterior portions of a palate-spanning aligner that serve to extinguish destructive oral habits.

Since a machined aligner can exhibit a wide range of thicknesses, the present invention anticipates varying the thickness of the material located over the occlusal surfaces of the teeth. In particular, additional thickness over the occlusal of the lower second molars for example can be useful in retarding or reducing the extent of eruption of the upper second molars. Head room located over the occlusal aspect of a molar tooth reserves empty space inside the tooth-receiving compartment which shelters the tooth from opposing occlusal forces. Such a configuration can serve to encourage full-eruption of a under erupted molar. These steps are part of an orthodontist's efforts at correcting closed bites.

Still other well-known structures used in orthodontics to advance the mandible from a Class II malocclusion into a Class I are enabled by machined aligners 70. For example, structures known as Twin Block camming or inter-working inclines can be CNC-machined into a pair of aligners. Such inclines are small inclined ramps located on the occlusal of the upper first molars and over the lower second bicuspids which serve to prevent a patient from fully closing unless the mandible is advanced forward. Over time, physiological responses to the continual forward posturing of the mandible elicits a physiological adaptation for a permanently more forward-positioned mandible.

As mentioned briefly earlier, CNC machines are often equipped with a feature known as a tool changer. A tool changer holds various types and sizes of cutting tools. The CNC machine will switch-out cutting tools on the fly as instructed by the CNC program. The CAD/CAM programming stage can involve the machining of alphanumeric characters on flat or curving surfaces of an aligner. Tool paths for the creation of numbers and letters are not significantly different than tool paths created for machining biological surfaces. A tool changer can hold a tool appropriately sized for engraving such as a 1/64 in. (0.0156 in.) diameter ball mill. It is feasible then for graphic symbols, sequential numbers indicating sequence of use, ID numbers of all sorts and the doctor's or patient's name to be CNC-engraved onto the surfaces of a CNC-machined aligner. Alphanumeric figures for example can be in positive (standing) configuration or negative (indented) configuration and placed anywhere for best positioning on an aligner.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A method for forming a thin-walled polymeric orthodontic aligner defined by opposing first and second sides, said method comprising:

creating a model of a patient's dental anatomy in a computer-aided design (CAD) system;

manipulating the CAD model to design an aligner to exert a therapeutic force on at least one of the patient's teeth;

generating a set of instructions for a CNC milling machine to mill the first side and second side of an aligner based on the CAD model;

producing a holding pattern by CNC milling machine using a set of instructions generated based on the CAD model to support at least a portion of the first side of the aligner;

providing a blank of polymeric material on a CNC milling machine;

milling the blank with the CNC milling machine to create the first side of the aligner;

supporting at least a portion of the first side on the holding pattern; and milling the blank with the CNC milling machine to create the second side of the aligner.

2. The method of claim 1 wherein selected regions of the aligner have different thicknesses between the first and second sides.

3. The method of claim 1 further comprising designing at least one feature in the CAD model of the aligner for accepting an aligner auxiliary.

4. The method of claim 1 further comprising designing at least one attachment point in the CAD model of the aligner for attaching other orthodontic components to the aligner.

5. The method of claim 1 further comprising designing a bump in the CAD model of the aligner for exerting a therapeutic force on a tooth.

6. The method of claim 1 further comprising designing a window in the CAD model of the aligner.

* * * * *